(12) United States Patent
Vissiere et al.

(10) Patent No.: US 11,191,455 B2
(45) Date of Patent: Dec. 7, 2021

(54) METHOD FOR ESTIMATING THE RELATIVE ORIENTATION BETWEEN A TIBIA AND A FEMUR

(71) Applicant: SYSNAV, Vernon (FR)

(72) Inventors: David Vissiere, Paris (FR); Mathieu Hillion, Vernon (FR); Adrien Rigaud, Vernon (FR); Laurent Geais, Romans sur Isere (FR)

(73) Assignee: SYSNAV, Vernon (FR)

( * ) Notice: Subject to any disclaimer, the term of this patent is extended or adjusted under 35 U.S.C. 154(b) by 425 days.

(21) Appl. No.: 16/310,351

(22) PCT Filed: Jun. 13, 2017

(86) PCT No.: PCT/FR2017/051523
§ 371 (c)(1),
(2) Date: Dec. 14, 2018

(87) PCT Pub. No.: WO2017/216476
PCT Pub. Date: Dec. 21, 2017

(65) Prior Publication Data
US 2019/0133498 A1    May 9, 2019

(30) Foreign Application Priority Data
Jun. 16, 2016   (FR) ...................................... 1655620

(51) Int. Cl.
*A61B 5/11*   (2006.01)
*A61B 5/107*   (2006.01)
(Continued)

(52) U.S. Cl.
CPC .......... *A61B 5/1121* (2013.01); *A61B 5/1071* (2013.01); *A61B 5/1122* (2013.01);
(Continued)

(58) Field of Classification Search
CPC ... A61B 5/1121; A61B 5/1122; A61B 5/1071; A61B 5/1124; A61B 5/4585;
(Continued)

(56) References Cited

U.S. PATENT DOCUMENTS 9,173,596 B1 * 11/2015 Berme ................. A61B 5/6828
2006/0245627 A1   11/2006 Nagamune
(Continued)

FOREIGN PATENT DOCUMENTS

| WO | 2005/104945 A2 | 11/2005 |
| WO | 2014/209916 A1 | 12/2014 |

OTHER PUBLICATIONS

David R. Labbe et al., Accounting for velocity of the pivot shift test manoeuvre decreases kinematic variability, The Knee, vol. 18, Issue 2, 2011, pp. 88-93, https://doi.org/10.1016/j.knee.2010.03.008. (Year: 2011).*

(Continued)

*Primary Examiner* — Eric F Winakur
*Assistant Examiner* — Marjan Fardanesh
(74) *Attorney, Agent, or Firm* — Womble Bond Dickinson (US) LLP (57) ABSTRACT

The present invention relates to a method for estimating the relative orientation between a tibia (11a) and a femur (11b) of a lower limb (10) of a person (1), the method being characterised in that it comprises the steps of:
(a) During at least one reference movement of said lower limb (10) from a reference position, acquiring by first inertial measuring means (20a) integral with the tibia (11a) and by second inertial measuring means (20b) integral with the femur (11b) reference accelerations and angular velocities;
(b) Estimating a plurality of morphological parameters of said lower limb (10), as a function of said measured reference accelerations and angular velocities;
(Continued)

(c) Determining a relative orientation in said initial position between said tibia (11a) and femur (11b), as a function of said estimated morphological parameters of said lower limb (10);
(d) During a working movement of said lower limb (10) from an initial position, acquiring by the first inertial measuring means (20a) and the second inertial measuring means (20b) working angular velocities;
(e) Estimating the relative orientation between said tibia (11a) and femur (11b) as a function of said measured working angular velocities, and of said relative orientation in said initial position.

15 Claims, 5 Drawing Sheets

(51) Int. Cl.
*A61B 5/00* (2006.01)
*A61B 90/00* (2016.01)
*A61F 2/38* (2006.01)

(52) U.S. Cl.
CPC .......... *A61B 5/1124* (2013.01); *A61B 5/4585* (2013.01); *A61B 5/6828* (2013.01); *A61B 2090/067* (2016.02); *A61B 2562/0219* (2013.01); *A61F 2/3859* (2013.01)

(58) Field of Classification Search
CPC ...... A61B 2562/0219; A61B 2090/067; A61B 5/1114; A61B 5/1116–1128; A61B 5/6828–6829; A61B 5/4571–4595; A61B 5/107–1135; A61L 35/1071
See application file for complete search history.

(56) References Cited

U.S. PATENT DOCUMENTS

| 2010/0312149 | A1 | 12/2010 | Hagemeister et al. |
| 2011/0213275 | A1 | 9/2011 | Boos et al. |
| 2013/0324890 | A1* | 12/2013 | Youssef ............... G01C 22/006 600/595 |
| 2014/0276886 | A1* | 9/2014 | Stein .................... A61B 5/4851 606/102 |

OTHER PUBLICATIONS

K. Liu, T. Liu, K. Shibata and Y. Inoue, "Visual estimation of lower limb motion using physical and virtual sensors," The 2010 IEEE International Conference on Information and Automation, Harbin, China, 2010, pp. 179-184, doi: 10.1109/ICINFA.2010.5512355. (Year: 2010).*

Preliminary Research Report received for French Application No. 1655620, dated Mar. 31, 2017, 3 pages (1 page of French Translation Cover Sheet and 2 pages of original document).

Labbe et al., "Accounting for velocity of the pivot shift test manoeuvre decreases kinematic variability", The Knee, vol. 18, 2011, pp. 88-93.

International Search Report and Written Opinion received for PCT Patent Application No. PCT/FR2017/051523, dated Nov. 2, 2017, 22 pages (10 pages of English Translation and 12 pages of Original Document).

International Preliminary Report on Patentability received for PCT Patent Application No. PCT/FR2017/051523, dated Dec. 27, 2018, 17 pages (9 pages of English Translation and 8 pages of Original Document).

* cited by examiner

METHOD FOR ESTIMATING THE RELATIVE ORIENTATION BETWEEN A TIBIA AND A FEMUR

GENERAL TECHNICAL FIELD

The present invention relates to the field of navigation applied to medical purposes.

More specifically, it relates to a method for estimating the relative orientation between a tibia and a femur of a lower limb of a patient.

PRIOR ART

The knee is a joint of the human body that is subject to severe stresses and unfortunately often suffers ligament injuries on account of not just playing sports but also daily life. In particular, the deterioration of the cruciate or collateral ligaments is a frequent cause of ligament intervention on the knee. In parallel to this, osteoarthritis and overweight are preponderant factors in the wear of the knee joint. This wear can end up in the replacement of the joint by implanting a prosthesis (arthroplasty).

Thus, orthopaedic surgery is for example used for the implantation of a knee prosthesis, partial or total, or a ligament reconstruction or replacement operation.

Each of these operations, but also their planning (preoperative diagnostic) or their later verification (postoperative consultation) requires the examination of the mobility of the knee.

If practitioners have frequently resorted to everyday tests (in particular the Lachman or Pivot-Shift tests) when it involves estimating notably the state of the cruciate ligaments, it has been noted that diagnostics based on these tests are very subjective.

Unless the Lachman and Pivot-Shift manipulations are standardised, by describing the directing protocols or thanks to motorised systems to control the applied force and torque profiles, the reduction in inter-operator disparity of ligament diagnostics is through the quantification of the test results by means of relevant variables.

Similarly, during a surgical prosthesis implant, cuts of the tibia and of the femur have to be made in clearly determined planes in order to adapt the bone to the shape of the prosthesis.

Thus, it appears necessary to determine a certain number of morphological parameters of the lower limb (such as the positions of reference anatomical points) and to know the relative orientation between the tibia 11a and the femur 11b of the lower limb 10 of a patient 1.

Figure 1A:
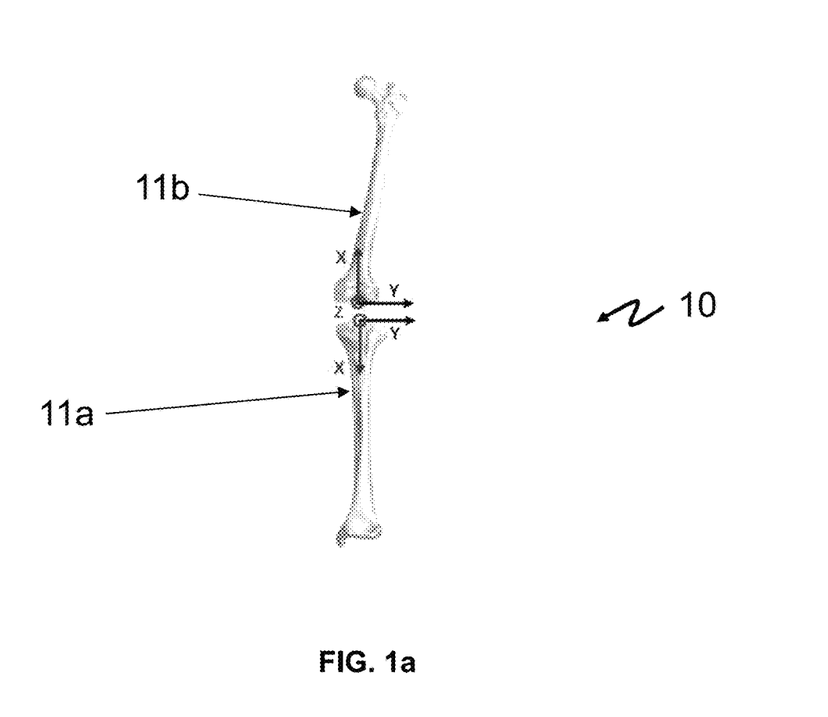
FIGS. 1a-1b represent tibial and femoral landmarks that can be used in the method according to the invention.

This is characterised by three anatomical angles, denoted respectively Flexion (flex), Varus (var) and Rotation (rot). The anatomical landmarks of a left lower limb 10 are thus illustrated by FIG. 1a.

For the left lower limb, they are defined (see FIG. 1b) as the angles making it possible to go from the femoral landmark to the tibial landmark by the following chain:
rotation of the angle 180°+flex around the mediolateral axis $y_f$ of the femoral landmark $(x_f, y_f, z_f)$, thereby creating a first intermediate landmark $(x_1, y_1, z_1)$;
rotation—of var around the axis $z_1$ of the first intermediate landmark, thereby creating a second intermediate landmark $(x_2, y_2, z_2)$,
rotation of—rot around the axis $x_2$ of the second intermediate landmark, ending up on the tibial landmark $(x_t, y_t, z_t)$.

Figure 1B:
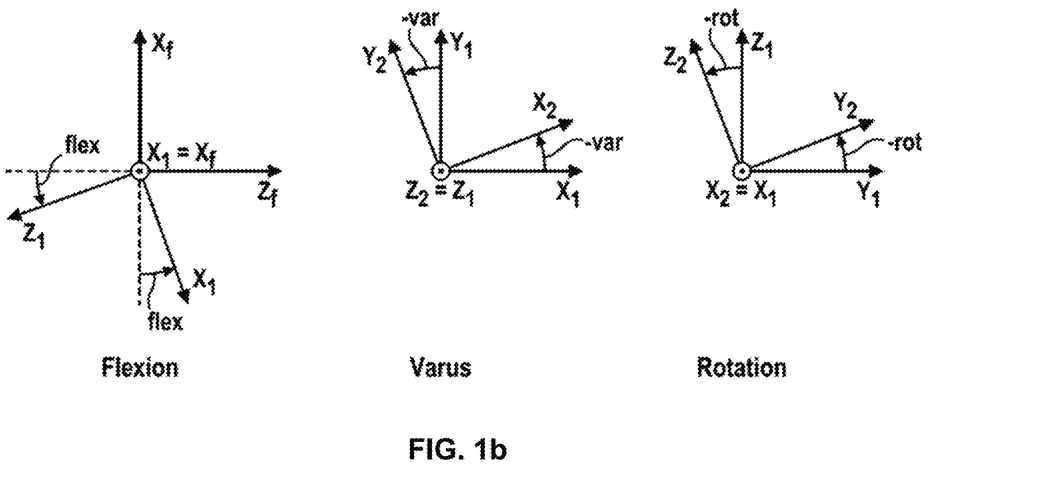

It will be understood that symmetrical landmarks may be constructed for the right lower limb.

Within the framework of this approach, studies have been carried out in order to analyse the relative movement of the tibia with respect to the femur. These studies may use magnetic sensors, inertial sensors or instead optical trackers.

However, none of them enable the identification of landmarks specific to the bones, which implies that the data are interpreted in a landmark dependent on the installation of the instrumentation.

In the field of surgery, products such as Smart Perseus of OrthoKey, KneeAlign of OrthoAlign or iAssist of Zimmer make it possible to guide femoral cuts. KneeAlign and iAssist also make it possible to guide tibial cuts. All three identify the mechanical axes using inertial sensors: gyrometers for Smart Perseus, accelerometers for KneeAlign and iAssist.

However, none of these products makes it possible to verify all the anatomical angles after the operation (or even before), hence the necessity of obtaining them by a radiography of the complete lower limb.

It would thus be desirable to have available a reliable, efficient and objectively reproducible method making it possible to obtain directly:
the tibial and femoral landmarks of a lower limb, notably making it possible to guide cutting during a resection of the tibia and/or of the femur;
their relative orientation in a reference position, typically the limb in hyper-extension, and to do so without it being necessary to carry out a verification radiography;
their relative orientation in the course of various consultation tests, notably making it possible to reconstruct information of movement of the limb of the patient in the anatomical axes:
The evolution of the anatomical angles of the knee (flexion, varus, rotation);
The angular velocity of the tibia relative to the femur;
The angular acceleration of the tibia relative to the femur;
The linear acceleration of the tibia;
The linear acceleration of the femur;
The relative translational linear acceleration between the tibia and the femur.

DESCRIPTION OF THE INVENTION

The present invention thus relates according to a first aspect to a method for estimating the relative orientation between a tibia and a femur of a lower limb of a person during a working movement of said lower limb from an initial position, the method being characterised in that it comprises the steps of:
(a) During at least one reference movement of said lower limb from a reference position having a same relative orientation between the tibia and the femur as the initial position, acquiring by first inertial measuring means integral with the tibia of said lower limb a reference acceleration and a reference angular velocity of said tibia, and acquiring by second inertial measuring means integral with the femur a reference acceleration and a reference angular velocity of said femur;
(b) Estimating by data processing means a plurality of morphological parameters of said lower limb, as a function of said measured reference accelerations and reference angular velocities;
(c) Determining by the data processing means a relative orientation in said initial position between said tibia and femur, as a function of said estimated morphological parameters of said lower limb;
(d) During said working movement of said lower limb from the initial position, acquiring by the first inertial measuring means a working angular velocity of said tibia, and acquiring by the second inertial measuring means a working angular velocity of said femur;
(e) Estimating by the data processing means the relative orientation between said tibia and femur as a function of said measured working angular velocities, and of said relative orientation in said initial position between said tibia and femur.

According to other advantageous and non-limiting characteristics:
step (c) comprises the determination from morphological parameters:
of a relative orientation between the first inertial measuring means and the tibia;
of a relative orientation between the second inertial measuring means and the femur;
of a relative orientation in said initial position between the first inertial measuring means and the second inertial measuring means;
from which is expressed said relative orientation in said initial position between said tibia and femur;
step (e) comprises the determination of the variation in relative orientation of the first inertial measuring means with respect to the initial position, and the determination of the variation in relative orientation of the second inertial measuring means with respect to the initial position, the relative orientation between said tibia and femur being given by the equation $$P_{t \to f}(t) = P_{bf \to f} P_{bf}{}^0{}_{\to bf}(t) P_{bt}{}^0{}_{\to bf}{}^0 P_{bt \to bt}{}^0(t) P_{t \to bt};$$

said plurality of estimated morphological parameters comprises the position of the centre of a knee of the lower limb, the position of the centre of a hip of the lower limb, the position of the centre of an ankle of the lower limb, the inter-malleolar direction of the ankle of the lower limb, and the average direction of rotation of the tibia with respect to the femur in the course of a flexion movement;
step (a) is implemented for at least one reference movement comprising the palpation of the lower limb by a tool so as to estimate via said palpation the position of the centre of a knee of the lower limb and/or the position of the centre of an ankle of the lower limb;
said plurality of estimated morphological parameters also comprises the mechanical axis of the femur, the mediolateral axis of the femur, the anteroposterior axis of the femur, the mechanical axis of the tibia, the mediolateral axis of the tibia, the anteroposterior axis of the tibia, estimated in step (b) from said position of the centre of the knee of the lower limb, position of the centre of the hip of the lower limb, position of the centre of the ankle of the lower limb, inter-malleolar direction of the ankle of the lower limb, and average direction of rotation of the tibia with respect to the femur in the course of a flexion movement.
the relative orientation between the first inertial measuring means and the tibia is determined from said mechanical axis of the tibia, mediolateral axis of the tibia and anteroposterior axis of the tibia;
the relative orientation between the second inertial measuring means and the femur is determined from said mechanical axis of the femur, mediolateral axis of the femur and anteroposterior axis of the femur;

the method comprises the implementation of step (a) for a plurality of reference movements of which at least:
a circular movement of the lower limb maintained rigid such that the orientation between the tibia and the femur is permanently identical to that in the initial position, the hip being maintained immobile;
a circular movement of a leg of the lower limb, the knee being maintained immobile;
a flexion movement of the lower limb.
said relative orientation in said initial position between the first inertial measuring means and the second inertial measuring means is determined by solving Wahba's problem during said circular movement of the lower limb maintained rigid;
the position of the centre of a knee of the lower limb and/or the position of the centre of a hip of the lower limb is estimated at step (b) as the centre of rotation of the first and/or of the second inertial measuring means in the course of one of said circular movements by the least squares resolution of an equation linking said measured reference accelerations and reference angular velocities;

According to a second aspect, the invention relates to equipment for estimating the relative orientation between a tibia and a femur of a lower limb of a person during a working movement of said lower limb from an initial position, characterised in that it comprises data processing means configured to implement:
a first module for receiving, during at least one reference movement of said lower limb from a reference position having a same relative orientation between the tibia and the femur as the initial position, a reference acceleration and a reference angular velocity of said tibia acquired by the first inertial measuring means integral with the tibia of said lower limb, and a reference acceleration and a reference angular velocity of said femur acquired by the second inertial measuring means integral with the femur;
a first module for estimating a plurality of morphological parameters of said lower limb, as a function of said measured reference accelerations and reference angular velocities;
a module for determining a relative orientation in said initial position between said tibia and femur, as a function of said estimated morphological parameters of said lower limb;
a second module for receiving, during said working movement of said lower limb from the initial position, a working angular velocity of said tibia acquired by the first inertial measuring means, and a working angular velocity of said femur acquired by the second inertial measuring means;
a second module for estimating the relative orientation between said tibia and femur as a function of said measured working angular velocities, and of said relative orientation in said initial position between said tibia and femur.

According to other advantageous and non-limiting characteristics:
The equipment is a box comprising the first or the second inertial measuring means;
The equipment is a mobile terminal or a server, suited to communicate with a first box comprising the first inertial measuring means and a second box comprising the second inertial measuring means.

According to a third aspect, the invention relates to a system comprising the equipment according to the second aspect of the invention and at least one first and one second box in connection.

According to a fourth and a fifth aspect, the invention relates to a computer programme product comprising code instructions for the execution of a method for estimating the relative orientation between a tibia and a femur of a lower limb of a person according to the first aspect of the invention; and a storage means that can be read by a computer equipment on which a computer programme product comprises code instructions for the execution of a method for estimating the relative orientation between a tibia and a femur of a lower limb of a person according to the first aspect of the invention.

DESCRIPTION OF THE FIGURES

Other characteristics and advantages of the present invention will become clear from reading the description that follows of a preferential embodiment. This description will be given with reference to the appended drawings in which:

FIGS. 4b-4c represent two steps of a reference movement using the palpation gripper according to FIG. 4a.

DETAILED DESCRIPTION

Architecture

Figure 2:
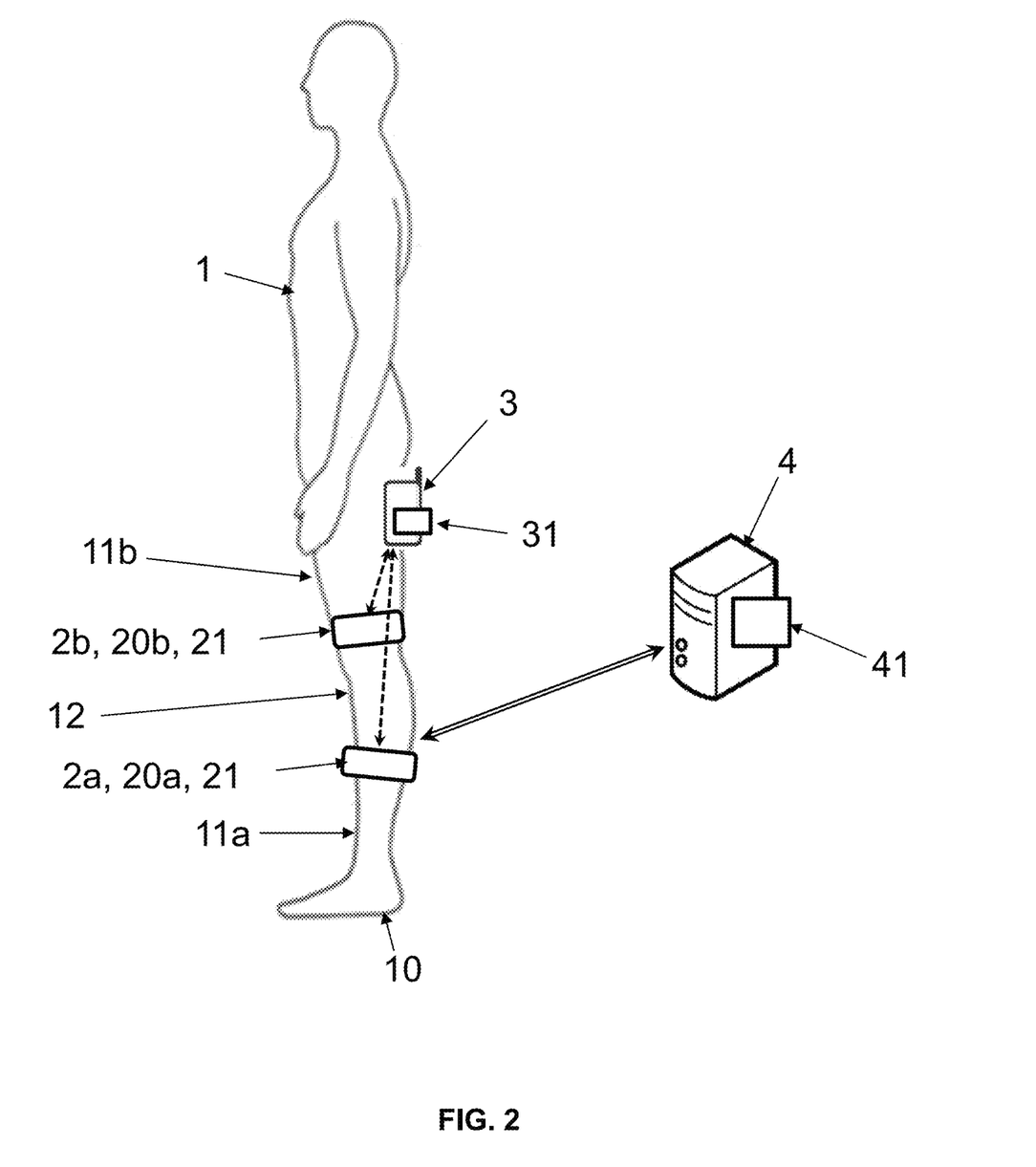
FIG. 2 is a diagram of equipment for the implementation of the method according to the invention.

With reference to FIG. 2, the present method makes it possible to estimate the relative orientation between a tibia 11a and a femur 11b of a lower limb 10 (i.e. a "leg" in common parlance, even if as will be seen later this designation is inappropriate, a leg anatomically designating "the lower leg", that is to say the part between the ankle and the knee 12) of a person 1. The person has at least this lower limb 10 equipped with first and second inertial measuring means 20a, 20b. It will be understood that each of the two lower limbs 10 of the person 1 may be equipped with these inertial measuring means 20a, 20b.

More specifically, the first inertial measuring means 20a are integral with the tibia 11a of this lower limb 10, and the second inertial measuring means 20b are integral with the femur 11b of this lower limb 10. In other words, in one case as in the other, they have a substantially identical movement in the terrestrial frame of reference, it will be seen how later.

In practice, the first inertial measuring means 20a are attached to the leg, that is to say as explained the lower half of the limb 10 which extends between the ankle and the knee 12 (they are thus considered integral with the tibia 11a), and the second inertial measuring means 20b are attached to the thigh, that is to say the upper half of the limb 10 which extends between the hip and the knee 12 (and they are thus considered integral with the femur 11b).

Figure 3:
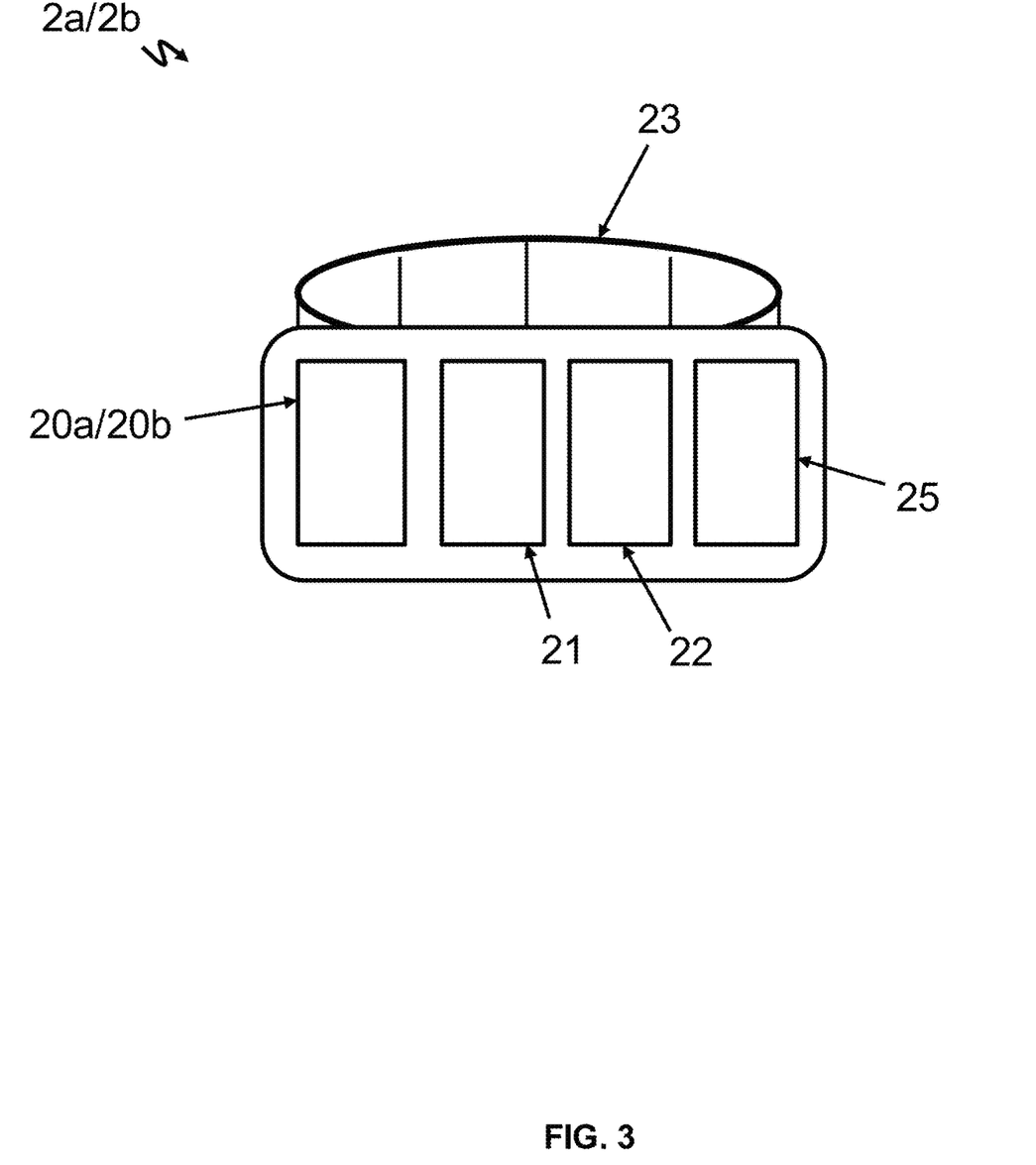
FIG. 3 represents in greater detail an example of box for the implementation of the method according to the invention.

In one case as in the other, the inertial measuring means 20a, 20b (as will be seen the two means 20a and 20b are advantageously identical) are preferentially those of a box 2a, 2b (similarly, the two boxes 2a and 2b respectively housing the means 20a and 20b are advantageously identical) as represented in FIG. 3 having means 23 for attachment to the lower limb 10. These attachment means 23 consist for example of a bracelet for example with a Velcro-fastener element which tightly hugs the limb and enables the integral connection thereof. As will be seen later, it is in fact desirable that the inertial measuring means 20a, 20b cannot move along the limb 10, nor turn around it.

By convention, the first box 2a will be called tibial box (bt), and the second box 2b will be called femoral box (bf).

The so-called femoral box landmark $R_{bf}$ is associated with the second box 2b (i.e. with the second inertial measuring means 20b), the so-called tibial box landmark $R_{bt}$ is associated with the first box 2a (i.e. with the first inertial measuring means 20a), the landmark $R_f$ is associated with the femur f, and the landmark $R_t$ is associated with the tibia t. For reasons of legibility, a box or a bone will be merged in the notations with its associated landmark (the notation bt could thus designate according to the context either the box bt or the landmark $R_{bt}$). The indices $bf^0$ and $bt^0$ designate a box (or its landmark) in its initial state (i.e. in a position designated initial position which will be described hereafter, at the start of a given movement).

Inertial measuring means 20a, 20b are taken to mean an inertial unit comprising at least three accelerometers and three gyrometers arranged in a tripod shape. The gyrometers measure the instantaneous angular velocity of the inertial unit with respect to the terrestrial frame of reference, noted $\vec{\Omega}$. The accelerometers are sensitive to external forces other than gravitational forces applied on the sensor, and make it possible to measure an acceleration noted $\vec{A}$.

One and/or the other of the boxes 2a, 2b (advantageously only one of the two which will be a main box) may comprise processing means 21 (typically a processor) for the implementation directly in real time of the processings of the present method, or instead the measurements may be transmitted via communication means 25 to an external device such as a mobile terminal (smartphone) 3, or even a remote server 4, or instead the measurements may be recorded in local memory data storage means 22 (a flash type memory for example) for a posteriori processing for example on the server 4.

The communication means 25 may implement a short range wireless communication, for example Bluetooth® or Wi-Fi™ (in particular in one embodiment with a mobile terminal 3), or even be means for connecting to a mobile network (typically UMTS/LTE™) for a long distance communication. It should be noted that the communication means 25 may be for example a wire connection (typically USB) to transfer the data from the local data storage means 22 to those of a mobile terminal 3 or a server 4.

If it is a mobile terminal 3 (respectively a server 4) that houses "the intelligence", it comprises processing means 31 (respectively 41) such as a processor for the implementation of the processings of the present method that are going to be described. When the processing means used are those 21 of a box 2a, 2b, said box may further include communication means 25 for transmitting the anatomical angles. For example, the anatomical angles may be sent to the mobile terminal 3 to display the angles in a navigation software interface.

In the remainder of the present description, it will be seen that the data processing means 21, 31, 41 respectively a box 2a, 2b, of a smartphone 3 and of a remote server 4 can indiscriminately and according to the applications carry out all or part of the steps of the method.

Principle and Notations

An orientation between two landmarks may be represented indiscriminately by a 3×3 matrix (9 components), by a quaternion (4 components) or by Euler angles (3 components). These objects have different mathematical properties but contain the same orientation information.

The anatomical angles as defined previously are Euler angles (YZX convention, for the order of the rotations), except for some adjustments of definitions (180° or signs). They have the advantage of drawing on terms that are common in the knee medicine field.

The sought-after orientation (relative orientation between the tibia 11a and the femur 11b) could thus be noted $P_{t \to f}$ (representation by a matrix), $q_{t \to f}$ (representation by a quaternion) or (flex, var, rot) (representation by the anatomical angles). In the remainder of this description, the example will be taken of the representation by a matrix, but those skilled in the art will be able to transpose it.

Assuming the velocity of rotation of a solid is known, the orientation of this solid follows the following kinematic:

$$\dot{q} = \frac{1}{2} q \, q_\omega$$

where:
q is the quaternion designating the absolute orientation of the solid $$q_\omega = \begin{bmatrix} 0 \\ \omega_x \\ \omega_y \\ \omega_z \end{bmatrix},$$

with $$\begin{bmatrix} \omega_x \\ \omega_y \\ \omega_z \end{bmatrix}$$

the velocity of rotation of the solid expressed in its local landmark.

This equation may be integrated to obtain the change of orientation $q_{t_2 \to t_1}$ of a solid between the two times $t_1$ and $t_2$.

During a movement of rotation of a point P around an immobile point O, the acceleration $\vec{A}$ and the velocity of rotation $\vec{\Omega}$ of the point P in the local landmark $R_P$ are linked by the formula:

$$[\vec{A}]_{R_P} = \frac{d[\vec{\Omega}]_{R_P}}{dt} \wedge [\overrightarrow{OP}]_{R_P} + [\vec{\Omega}]_{R_P} \wedge [\vec{\Omega}]_{R_P} \wedge [\overrightarrow{OP}]_{R_P}$$

Gyrometers fixed on P measure the velocity of rotation of the point P in the landmark $R_P$.

Accelerometers fixed on P do not measure directly the acceleration of P, but are also sensitive to the gravity field $\vec{g}$; they measure $\vec{\Gamma} = \vec{A} - \vec{g}$.

Finally, the accelerometric $\vec{\Gamma}_P$ and gyrometric $\vec{\Omega}_P$ data of a point P are linked by the relation:

$$\vec{\Gamma}_P + \vec{g} = \left( \frac{d\vec{\Omega}_P}{dt} + \vec{\Omega}_P \wedge \vec{\Omega}_P \right) \wedge [\overrightarrow{OP}]_{R_P}$$

These equations, as will be seen, are going to be applied to the accelerometric and gyrometric data of the first and second inertial measuring means 20a, 20b.

Method

The objective of the present method is to follow the relative orientation between the tibia 11a and the femur 11b of the patient 1 over the course of time. In a preferred manner, using the matrices, the one representing said relative orientation (noted $P_{t \to f}(t)$) is given at each instant by the equation:

$$P_{t \to f}(t) = P_{bf \to f} P_{bf^0 \to bf}(t) P_{bt^0 \to bf^0} P_{bt \to bt^0}(t) P_{t \to bt}$$

Where the passage matrices noted in bold type are constant (since each box 2a, 2b integral with the tibia 11a/femur 11b is considered), and represent respectively:
- a relative orientation ($P_{t \to bt}$) between the first inertial measuring means 20a and the tibia 11a,
- a relative orientation ($P_{bf \to f}$) between the second inertial measuring means 20b and the femur 11b,
- a relative orientation in said initial position ($P_{bt^0 \to bf^0}$) between the first inertial measuring means 20a and the second inertial measuring means 20b.

The present method is composed of two main phases, which will now be introduced.

The first phase consists in obtaining the initial relative orientation of the tibia with respect to the femur, that is to say in a so-called initial position. This initial position may be chosen arbitrarily, but it must be able to be maintained and repeated with precision. It may be carried out naturally (preferably, it is a position in which the lower limb is in hyper-extension, in particular that where the limb is flat on a support) or by means of a mechanical tool which makes it possible to force the lower limb into this position.

Indeed, the preceding equation of the orientation evaluated in 0 gives:

$$P_{t \to f}(0) =$$

$$P_{bf \to f} P_{bf^0 \to bf}(0) P_{bt^0 \to bf^0} P_{bt \to bt^0}(0) P_{t \to bt} = P_{bf \to f} P_{bt^0 \to bf^0} P_{t \to bt}$$

This phase advantageously makes it possible (it will be seen how later) to identify these constant matrices of the equation; namely the orientation of the femur with respect to its box ($P_{bf \to f}$), that of the tibia with respect to its box ($P_{t \to bt}$), and the initial relative orientation (at the start of the movement) between the two boxes ($P_{bt^0 \to bf^0}$).

It should be noted that the present method also involves at least one so-called reference position, which corresponds to a position having the same relative orientation between the tibia 11a and the femur 11b as the initial position, in other words a position which potentially only differs from the initial position by rotations and/or translations of the entire lower limb 10. The reference positions thus form a family of positions.

If the initial position corresponds to a hyper-extension, any reference position thus also corresponds to a hyper-extension.

The second phase consists in obtaining the changes of the relative orientation in the course of a given movement. To do so, the dynamic matrices of the present orientation equation are identified; namely the changes of orientation of each of the boxes ($P_{bf^0 \to bf}(t)$, in other words the variation in relative orientation of the second inertial measuring means 20b with respect to the initial position, and $P_{bt \to bt^0}(t)$, in other words the variation in relative orientation of the first inertial measuring means 20a with respect to the initial position) in the course of the movement.

It should be noted that the present method preferably only uses the data derived from inertial measurements (accelerations and/or angular velocities), for example not magnetic measurements.

Phase 1

In a first step (a), the method comprises, during at least one reference movement of said lower limb 10 from a reference position (as explained a position having the same relative orientation between the tibia 11a and the femur 11b as the initial position), the acquisition by the first inertial measuring means 20a of a reference acceleration and of a reference angular velocity of said tibia 11a, and the acquisition by the second inertial measuring means 20b of a reference acceleration and of a reference angular velocity of said femur 11b.

These accelerations and angular velocities are designated "reference" since measured during a reference movement, that is to say a predetermined movement (examples of reference movements, also called "manipulations" will be described hereafter), as opposed to accelerations and angular velocities designated "working" or "test", which will be measured during any movement of the lower limb 10 from the initial position, that is to say a given movement during which the evolution of the relative orientation between the tibia 11a and the femur 11b is unknown, and is sought. In practice, reference or working accelerations and angular velocities are acquired in exactly the same way.

These magnitudes are advantageously measured with a dt sampling (i.e. every "dt" seconds) with dt very small compared to the characteristic times of the movements of the patient 1, typically 8 ms.

In a step (b), the data processing means 21, 31, 41 estimate a plurality of morphological parameters of said lower limb 10, as a function of said measured reference accelerations and reference angular velocities.

As explained, said morphological parameters designate anatomical magnitudes describing the tibia 11a and/or the femur 11b, and consist typically of a vector expressed in a given landmark.

In particular, the following could be cited:
the position of the centre of the knee 12 (the middle of the epicondyles);
the position of the centre of the hip (the centre of rotation of the lower limb 10 in the course of circular movements of the lower limb, the knee 12 being maintained fixed in the course of these movements);
the position of the centre of the ankle (the middle of the malleoli);
the inter-malleolar direction (the direction linking the medial malleolus to the lateral malleolus of the ankle);
the average direction of rotation of the tibia 11a with respect to the femur 11b in the course of a flexion movement of the lower limb 10;
the mechanical axis of the femur 11b (the direction linking the centre of the knee 12 to the centre of the hip of the lower limb 10);
the mediolateral axis of the femur 11b (the projection, on the plane orthogonal to the mechanical axis of the femur, of the relative average direction of rotation in the course of a flexion movement);
the anteroposterior axis of the femur 11b (vectorial product of the mechanical axis and the mediolateral axis);
the mechanical axis of the tibia 11a (the direction linking the centre of the knee 12 to the centre of the ankle of the lower limb);
the mediolateral axis of the tibia 11a (the projection on the plane orthogonal to the mechanical axis of the tibia 11a of the direction linking the medial malleolus to the lateral malleolus of the ankle);
the anteroposterior axis of the tibia 11a (vectorial product of the mechanical axis and the mediolateral axis).

It should be noted that certain morphological parameters may be estimated "indirectly", that is to say themselves from other morphological parameters (typically the mechanical axes of the femoral and tibial landmarks, from knee/hip/ankle positions).

Advantageously, at least the position of the centre of the knee 12, the position of the centre of the hip, the position of the centre of the ankle, or even the inter-malleolar direction and the average direction of rotation of the tibia 11a with respect to the femur 11b in the course of a flexion movement are morphological parameters estimated directly.

The other morphological parameters (the mechanical axis of the femur 11b, the mediolateral axis of the femur 11b, the anteroposterior axis of the femur 11b, the mechanical axis of the tibia 11a, the mediolateral axis of the tibia 11a, the anteroposterior axis of the tibia 11a) are typically obtained entirely or partially from the preceding parameters.

As will be seen, step (a) is preferentially implemented for a plurality of reference movements (advantageously at least three, preferentially four), such that during each of them reference accelerations and angular velocities are acquired. In other words, step (a) thus advantageously makes it possible to acquire a plurality of sets of measured reference accelerations and angular velocities (tibia/femur), each associated with a reference movement.

It should be noted that if it is necessary that at least one reference movement is carried out from a reference position, this is not necessary for all of the additional movements which can, for the most part, be carried out from any position.

The reference accelerations and angular velocities measured for each reference movement enable the estimation of one or more parameters of said plurality of morphological parameters of the lower limb 10.

Reference Movements

As will be seen, certain morphological parameters may be estimated either by calculation from reference accelerations and angular velocities, or directly by palpation of characteristic points of the lower limb 10 (i.e. physical positioning thanks to a tool "touching" the lower limb 10 precisely at the level of these characteristic points, which are typically the malleoli or the epicondyles) during certain reference movements.

The five reference movements that will now be described constitute five efficient examples because they are simple and reproducible, and it is not necessary to accomplish them all (some are alternatives). Those skilled in the art will know how to use other movements instead of these.

Reference Movement 1: Palpation of the Malleoli

This manipulation (between a time $t_1$ and a time $t_2$) makes it possible to identify the following morphological parameters:

$[C_tO_c]_{bt}$: Centre-Ankle in the landmark of the tibial box;

$[\overrightarrow{u_{M_1M_2}}]_{bt}$: Inter-malleolar direction in the landmark of the tibial box.

Figure 4A:
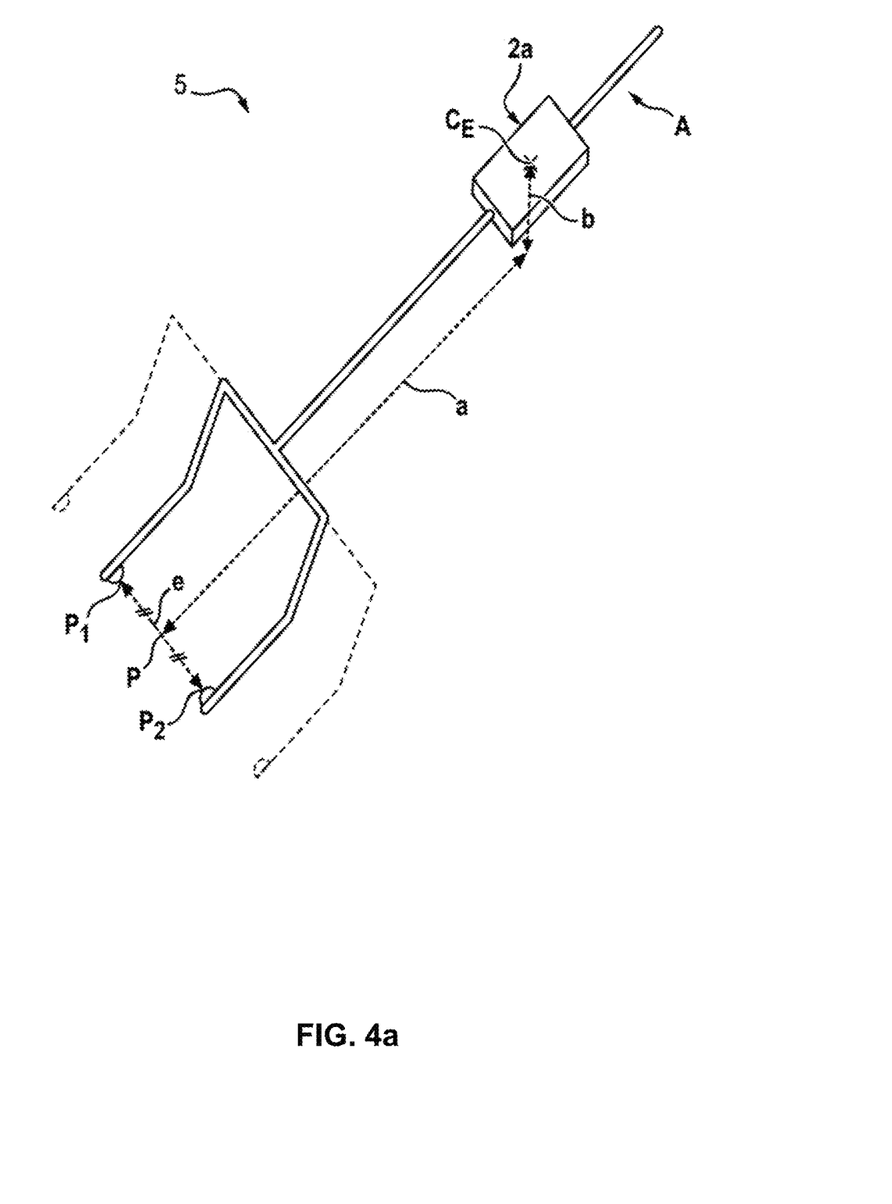
FIG. 4a represents an example of palpation gripper for the implementation of a preferred embodiment of the method according to the invention.

One means for obtaining these elements is to use a mechanical gripper 5 as illustrated in FIG. 4a. It is equipped with two malleolar feelers P1 and P2 spaced apart by a distance e and is able to cooperate with, i.e. to be temporarily integral with, the first inertial measuring means 20a (more specifically the first box 2a). On such a gripper 5, the width e is adjustable and the vectors $[C_tA]_{bt}$ and $[C_tP]_{bt}$, where A designates the end of the gripper 5, are data of the problem.

At the time $t_1$ (see FIG. 4b):
The feelers P1 and P2 are in contact with the malleoli;
The point $O_c$ (Centre-Ankle) is merged with the middle of the feelers P which is a datum of the problem;
The direction $\vec{u}_{M_1M_2}$ coincides with the direction linking the feelers $\vec{u}_{P_1P_2}$ which is a datum of the problem.

At the time $t_2$ (see FIG. 4c):
The first box 2a is placed in its definitive position with respect to the tibia 11a (and attached thereafter to the leg thanks to the attachment means 23), the point A having remained immobile with respect to the leg of the patient between the times $t_1$ and $t_2$.

Figure 4B:
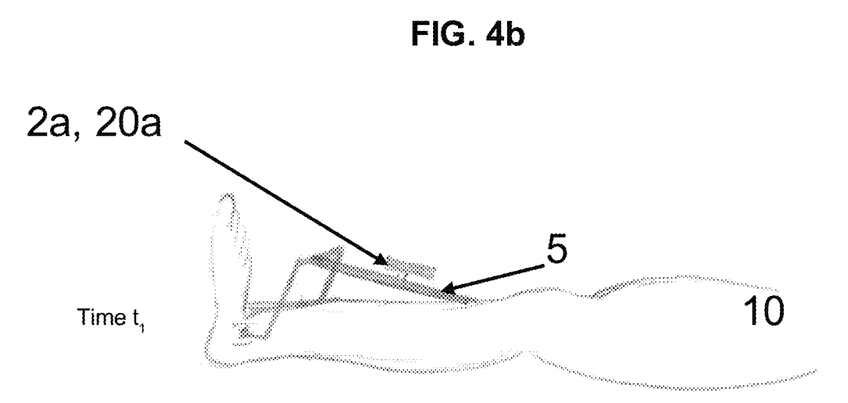
Figure 4C:
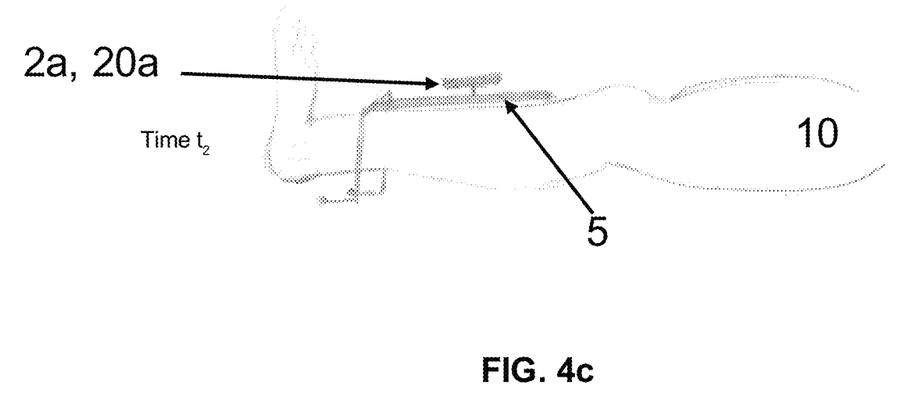

The equation $$\dot{q} = \frac{1}{2} q \, q_\omega$$

may be used to determine the change of orientation $P_{bt^1 \to bt^2}$ of bt between the times $t_1$ and $t_2$.

Thus if:
The lower limb 10 is immobile between the times $t_1$ and $t_2$,
The first inertial measuring means 20a are in pure movement of rotation around the point A between the times $t_1$ and $t_2$
The first inertial measuring means 20a are immobile with respect to the leg for $t > t_2$ (i.e. attached via the attachment means 23, in other words they have a character integral with the tibia 11a for $t > t_2$, Then the two sought-after morphological parameters are expressed in the landmark of the tibial box $R_{bt}$ by:

$$\begin{cases} [C_tO_c]_{bt} = [C_tA]_{bt} + P_{bt^1 \to bt^2}[AP]_{bt} \\ [\vec{u}_{M_1M_2}]_{bt} = P_{bt^1 \to bt^2}[\vec{u}_{P_1P_2}]_{bt} \end{cases}$$

Where, $P_{bt^1 \to bt^2}$ stems from the measured reference accelerations and angular velocities.

It should be noted that the starting position of the lower limb 10 for this movement is not important.

Reference Movement 2: Centre-Hip

This reference movement makes it possible to identify:
$[C_fO_h]_{bf}$: Centre-Hip in the landmark of the femoral box;
$[C_tO_h]_{bt}$: Centre-Hip in the landmark of the tibial box;
$P_{bt^0 \to bf^0}$: Harmonisation matrix.

This reference movement, carried out from a reference position, typically corresponds to a circular movement on the lower limb 10, the lower limb 10 being maintained rigid such that the relative orientation between the tibia 11a and the femur 11b is permanently identical to that in the reference position (i.e. that in the initial position), and the hip being maintained immobile in the course of the movements.

It is considered that the first and second inertial measuring means 20a, 20b (i.e. the two boxes bf and bt) are at each instant in rotational movement around a fixed point, merged with the Centre-Hip $O_h$.

The equation linking the accelerometric and gyrometric data proposed at the start then gives:

$$\begin{cases} \sum_k (\vec{\Gamma}_{bt}(k) + \vec{g}) = \sum_k \left( \frac{d\vec{\Omega}_{bt}}{dt}(k) + \vec{\Omega}_{bt}(k) \wedge \vec{\Omega}_{bt}(k) \right) \wedge [\overrightarrow{O_hC_t}]_{bt} \\ \sum_k (\vec{\Gamma}_{bf}(k) + \vec{g}) = \sum_k \left( \frac{d\vec{\Omega}_{bf}}{dt}(k) + \vec{\Omega}_{bf}(k) \wedge \vec{\Omega}_{bf}(k) \right) \wedge [\overrightarrow{O_hC_f}]_{bf} \end{cases}$$

In practice one identifies:

$$\begin{cases} [\overrightarrow{O_hC_t}]_{bt} = \arg\min_x \left( \left\| \sum_k (\vec{\Gamma}_{bt}(k) + \vec{g}) - \right. \right. \\ \left. \left. \sum_k \left( \frac{d\vec{\Omega}_{bt}}{dt}(k) + \vec{\Omega}_{bt}(k) \wedge \vec{\Omega}_{bt}(k) \right) \wedge \vec{X} \right\|^2 \right) \\ [\overrightarrow{O_hC_f}]_{bf} = \arg\min_x \left( \left\| \sum_k (\vec{\Gamma}_{bf}(k) + \vec{g}) - \right. \right. \\ \left. \left. \sum_k \left( \frac{d\vec{\Omega}_{bf}}{dt}(k) + \vec{\Omega}_{bf}(k) \wedge \vec{\Omega}_{bf}(k) \right) \wedge X \right\|^2 \right) \end{cases}$$

In addition, in the course of these same movements, since the first and second inertial measuring means 20a, 20b are integral with a same non-deformable solid (the lower limb 10 is assumed rigid), they undergo the same rotation velocities. The relative orientation between the tibia 11a and the femur 11b verifies at each instant:

$$\Omega_{bf}(t) = P_{bt \to bf} \Omega_{bt}(t), \forall t,$$

With $P_{bt \to bf} = \text{constant} = P_{bt^0 \to bf^0}$ (since the lower limb 10 is rigid)

This equation may be solved by using the solution to Wahba's problem. It is also possible to solve the least squares problem on the space of the matrices and next extract from the solution a relevant rotation matrix.

Reference Movement 3: Centre-Knee

This movement makes it possible to identify:
$[C_tO_g]_{bt}$: Centre-Knee in the landmark of the tibial box.

This reference movement typically corresponds to a circular movement with the leg of the patient 1, the knee (and thus the thigh) being maintained fixed during these movements. The starting position of the lower limb 10 has no importance for this movement.

It is considered that bt is at each instant in rotational movement around a fixed point, merged with the Centre-Knee $O_g$.

The equation linking the accelerometric and gyrometric data proposed at the start gives:

$$\sum_k (\vec{\Gamma}_{bt}(k) + \vec{g}) = \sum_k \left( \frac{d\vec{\Omega}_{bt}}{dt}(k) + \vec{\Omega}_{bt}(k) \bigwedge \vec{\Omega}_{bt}(k) \right) \bigwedge [\overrightarrow{O_gC_t}]_{bt}$$

In practice one identifies:

$$[\overrightarrow{O_gC_t}]_{bt} =$$

$$\arg\min_X \left( \left\| \sum_k (\vec{\Gamma}_{bt}(k) + \vec{g}) - \sum_k \left( \frac{d\vec{\Omega}_{bt}}{dt}(k) + \vec{\Omega}_{bt}(k) \bigwedge \vec{\Omega}_{bt}(k) \right) \bigwedge \vec{X} \right\|^2 \right)$$

Reference Movement 4: Flexion

This movement makes it possible to identify:

[$\overrightarrow{u_{\Omega_{t/f}}}$]$_{bf}$: Average direction of rotation of the tibia 11a with respect to the femur 11b in the course of a flexion movement (ranging for example from 40° to 80°), in the landmark of the femoral box.

The movement consists in carrying out a flexion movement of the lower limb 10, starting from a reference position, and covering at the flexion angle the range [40°; 80°].

The angle on which the data are selected (range [40°; 80°]) is extracted from the relative orientation of the boxes, given by:

$$P_{bt \to bf}(t) = P_{bf}^{REF \to bf}(t) P_{bt}^{REF \to bf}{}^{REF} P_{bt \to bt}^{REF}(t)$$

Since the movement starts from a reference position, the matrix $P_{bf}^{REF \to bf}{}^{REF} = P_{bt}{}^0 \to bf^0$ is known (identified thanks to the reference movement 2). The matrices $P_{bf^0 \to bf}(t)$ and $P_{bt \to bt^0}(t)$ are obtained from reference accelerometric and gyrometric data.

The knowledge of $P_{bt \to bf}(t)$ gives $\widetilde{flex}(t)$, an approximation of the angle of flexion in the course of the movement, and makes it possible to obtain the times $t^{40°}$ and $t^{80°}$.

Since the boxes bf and bt are integral with their respective bones, the relative velocity of rotation between the bones is merged with the relative velocity of rotation between the boxes.

The relative velocity of rotation is expressed at each instant in bf by:

$$[\Omega_{f/t}]_{bf}(t) = P_{bt \to bf}(t)[\Omega_{bt}(t)]_{bt} - [\Omega_{bf}(t)]_{bf}$$

Finally, [$\overrightarrow{u_{\Omega_{t/f}}}$]$_{bf}$ is obtained by the equation $$\langle \overrightarrow{u_{\Omega_{t/f}}} \rangle = \frac{\int_{t^{40°}}^{t^{80°}} \overrightarrow{u_{\Omega_{t/f}}}(t)dt}{\left\| \int_{t^{40°}}^{t^{80°}} \overrightarrow{u_{\Omega_{t/f}}}(t)dt \right\|},$$

where $\overrightarrow{u_{\Omega_{t/f}}} = \frac{\overrightarrow{\Omega_{t/f}}}{\|\overrightarrow{\Omega_{t/f}}\|}$ Reference Movement 5: Palpation of the Epicondyles This movement makes it possible to identify:

[$C_fO_g$]$_{bf}$: Centre-Knee in the landmark of the femoral box.
This movement is analogous to the movement 1, with:
The second box 2b in the role of the first box 2a
The epicondyles in the role of the malleoli
The Centre-Knee in the role of the Centre-Ankle
The equation $[C_tO_c]_{bt} = [C_tA]_{bt} + P_{bt^1 \to bt^2}[AP]_{bt}$ then becomes:

$$[C_fO_g]_{bf} = [C_fA]_{bf} P_{bf^1 \to bf^2}[AP]_{bf}$$

As will be seen, not all of these reference movements are indispensable, and those skilled in the art will be able to modify some of them as they see fit so as to obtain the morphological parameters of their choice.

In a preferred manner, at least the reference movements 2, 3 and 4 are carried out, at least the movements 2 and 4 being from a reference position (the movement 4 being accomplished after the movement 2). The case of the reference movements 1 and 5 is particular because they require a gripper 5, and preferably at least one of the two is carried out (if need be as first reference movement).

Initial Relative Orientation Between the Tibia and Femur

In a step (c), the data processing means 21, 31, 41 determine said relative orientation in said initial position between said tibia 11a and femur 11b (or rather its three components), as a function of said estimated morphological parameters of said lower limb 10.

Obtaining $P_{bt^0 \to bf^0}$

As explained, during any movement starting from the initial position and in which the lower limb 10 is rigid the following applies:

$$P_{bt \to bf} = \text{constant} = P_{bt^0 \to bf^0}$$

This constant is denoted harmonisation matrix and is determined thanks to the reference movement 2. It may be noted that the harmonisation matrix is a morphological parameter used "as such".

Obtaining $P_{t \to bt}$

The mechanical tibial axis $x_t$ is defined by the direction linking the centre of the knee 12 to the centre of the ankle:

$$x_t = \frac{\overrightarrow{O_gO_c}}{\|\overrightarrow{O_gO_c}\|}$$

This direction is obtained by localising these two points with respect to the centre of the first box 2a $C_t$:

$$[x_t]_{bt} = \frac{[\overrightarrow{O_gC_t}]_{bt} + [\overrightarrow{C_tO_c}]_{bt}}{\|\overrightarrow{O_gO_c}\|}$$

An estimation of the mediolateral tibial axis $y_t$ is given by the inter-malleolar direction linking the medial malleolus to the lateral malleolus:

$$[\tilde{y}_t]_{bt} = [\overrightarrow{u_{M_1M_2}}]_{bt} = \frac{[\overrightarrow{M_1M_2}]_{bt}}{\|\overrightarrow{M_1M_2}\|}$$

The mediolateral tibial axis is defined by the projection of its estimation $\tilde{y}_t$ in the plane orthogonal to $x_t$:

$$y_t = \frac{\tilde{y}_t - (\tilde{y}_t, x_t)x_t}{\|\tilde{y}_t - (\tilde{y}_t, x_t)x_t\|}$$

The third axis of the tibial landmark is defined by the vectorial product of the two other vectors:

$$z_t = x_t \wedge y_t$$

The matrix of orientation $P_{t \to bt}$ is then given by:

$$P_{t \to bt} = [[x_t]_{bt}|[y_t]_{bt}|[z_t]_{bt}]$$

The identification of $P_{t \to bt}$ thus requires the identification of the following three morphological parameters:

[$\overrightarrow{O_gC_t}$]$_{bt}$: Centre-Knee in the landmark of the tibial box (estimated via the reference movement 3)

[$\overrightarrow{C_tO_c}$]$_{bt}$: Centre-Ankle in the landmark of the tibial box (estimated via the reference movement 1)

[$\overrightarrow{u_{M_1M_2}}$]$_{bt}$: Inter-malleolar direction in the landmark of the tibial box (estimated via the reference movement 1)

Obtaining $P_{f \to bf}$

The mechanical femoral axis $x_f$ is defined by the direction linking the centre of the knee 12 to the centre of the hip:

$$x_f = \frac{\overrightarrow{O_g O_h}}{\|\overrightarrow{O_g O_h}\|}$$

This direction may be obtained by localising these two points with respect to the centre of the second box $2b$ $C_f$:

$$[x_f]_{bf} = \frac{[\overrightarrow{O_g C_f}]_{bf} + [\overrightarrow{C_f O_h}]_{bf}}{\|\overrightarrow{O_g O_h}\|}$$

or instead with respect to the centre of the first box $2a$ $C_t$, when the lower limb 10 is in the initial position:

$$[x_f]_{bf} = P_{bt^0 \to bf^0} \frac{[\overrightarrow{O_g C_t}]_{bt} + [\overrightarrow{C_t O_h}]_{bt^0}}{\|\overrightarrow{O_g O_h}\|}$$

An estimation $\tilde{y}_f$ of the mediolateral femoral axis is given by the average direction of rotation of the tibia with respect to the femur over a flexion range close to $[40°, 80°]$:

$$\tilde{y}_f = \langle \overrightarrow{u_{\Omega_{t/f}}} \rangle = \frac{\int_{40°}^{80°} \overrightarrow{u_{\Omega_{t/f}}}(t) dt}{\left\| \int_{40°}^{80°} \overrightarrow{u_{\Omega_{t/f}}}(t) dt \right\|},$$

$$\overrightarrow{u_{\Omega_{t/f}}} = \frac{\overrightarrow{\Omega_{t/f}}}{\|\overrightarrow{\Omega_{t/f}}\|}$$

where

The mediolateral femoral axis $y_f$ is defined by the projection of its estimation $\tilde{y}_f$ in the plane orthogonal to $x_f$:

$$y_f = \frac{\tilde{y}_f - (\tilde{y}_f, x_f) x_f}{\|\tilde{y}_f - (\tilde{y}_f, x_f) x_f\|}$$

The third axis of the femoral landmark is defined by the vectorial product of the two other data:

$z_f = x_f \wedge y_f$

The matrix of orientation $P_{bf \to f}$ is given by:

$$P_{bf \to f} = \begin{bmatrix} [x_f]_{bf} \\ [y_f]_{bf} \\ [z_f]_{bf} \end{bmatrix}$$

The identification of $P_{bf \to f}$ thus goes through the identification of the following three anatomical elements:

- $[\overrightarrow{O_g C_f}]_{bf}$: Centre-Knee in the landmark of the femoral box (estimated via the reference movement 5);
- $[\overrightarrow{C_f O_h}]_{bf}$: Centre-Hip in the landmark of the femoral box (estimated via the reference movement 2);
- $[\overrightarrow{u_{\Omega_{t/f}}}]_{bf}$: Average direction of rotation of the tibia 11a with respect to the femur 11b in the course of a flexion movement ranging from 40° to 80°, in the landmark of the femoral box (estimated via the reference movement 4)

or instead by that of the following four anatomical elements:

- $[\overrightarrow{O_g C_f}]_{bt}$: Centre-Knee in the landmark of the tibial box (estimated via the reference movement 3)
- $[\overrightarrow{C_f O_h}]_{bt}$: Centre-Hip in the landmark of the tibial box (estimated via the reference movement 2)
- $P_{bt^0 \to bf^0}$: Relative orientation between the tibial box and the femoral box (i.e. between the first and second inertial measuring means 20a, 20b) in the initial position, denoted harmonisation matrix (estimated via the reference movement 2)
- $[\overrightarrow{u_{\Omega_{t/f}}}]_{bf}$: Average direction of rotation of the tibia 11a with respect to the femur 11b in the course of a flexion movement ranging from 40° to 80°, in the landmark of the femoral box (estimated via the reference movement 4)

Phase 2

Once said relative orientation in said initial position between said tibia 11a and femur 11b (and more specifically its components $P_{t \to bt}$, $P_{bf \to f}$ and $P_{bf^0 \to bt^0}$) has been determined, then a working movement (that is to say as explained a movement from the initial position which is not a reference, that is to say any non-predetermined position, and for which it is sought to know the relative orientation between the tibia 11a and the femur 11b) is carried out.

In a step (d), during the working movement of said lower limb 10 from said initial position, the first inertial measuring means 20a acquire a working angular velocity of said tibia 11a, and the second inertial measuring means 20b acquire a working angular velocity of said femur 11b. It may be noticed that advantageously no working acceleration is acquired, but it is entirely possible to acquire a working acceleration of the tibia 11a and a working acceleration of the femur 11b (which makes it possible not to change the configuration of the inertial measuring means 20a, 20b with respect to step (a)); such working accelerations not being used in the remainder of the calculation.

Thus, this step (d) is advantageously implemented in a manner similar to step (a).

Finally, in a step (e), the data processing means 21, 31, 41 estimate the relative orientation between said tibia 11a and femur 11b as a function of said measured working angular velocities, and of said relative orientation in said initial position between said tibia 11a and femur 11b.

More specifically, the matrices of the equation $P_{t \to f}(t) = P_{bf \to f} P_{bf^0 \to bf}(t) P_{bt^0 \to bf^0} P_{bt \to bt^0}(t) P_{t \to bt}$, which are time-dependent, are identified.

Thus, the matrix $P_{bt \to bt^0}(t)$ represents the change of orientation of the first inertial measuring means 20a (tibial box bf) between the initial position, and the time t.

It is obtained by integrating the equation $$\dot{q} = \frac{1}{2} q q_\omega$$

between the times $t_0$ and t, from the working tibial angular velocity.

Similarly, the matrix $P_{bf \to bf^0}(t)$ represents the change of orientation of the second inertial measuring means 20b (femoral box bf) between the initial position, and the time t.

It is obtained by integrating the equation $$\dot{q} = \frac{1}{2} q q_\omega$$

between the times $t_0$ and $t$, from the working femoral angular velocity.

Applications—Phase 3

Preferably, the present method comprises a phase 3 (in the form of a step (f)) of exploitation of the estimated orientation for medical purposes.

Application 1: Cutting Guide

Once the matrices $P_{os \to b}$ ($P_{bf \to f}$ and $P_{t \to bt}$) are known, the orientation $P_{gc \to b}$ of a cutting guide with respect to a box $2a$, $2b$ makes it possible to obtain the orientation $P_{gc \to os}$ of the guide with respect to the bone:

$$P_{gc \to os}(t) = P_{b \to os} P_{gc \to b}(t)$$

The orientation $P_{gc \to b}$ may be identified through additional inertial measuring means (in a dedicated box bgc), integral with the cutting guide gc; thus, the above equation becomes:

$$P_{gc \to os}(t) = P_{b \to os} P_{bgc \to b}(t) P_{gc \to bgc}$$

where:

$P_{b \to os}$ has been identified in step (c);

$P_{gc \to bgc}$ is a datum of the problem.

Application 2: Information of Movements in the Anatomical Landmarks

Once the matrices $P_{t \to bt}$, $P_{f \to bf}$ and $P_{t \to f}(t)$ have been obtained, the movement information may be expressed in the tibial or femoral anatomical landmarks.

As an example, the velocity of rotation of the tibia $11a$ with respect to the femur $11b$ is expressed:

In the femoral landmark by:

$$[\Omega_{t/f}]_f(t) = P_{t \to f}(t) P_{bt \to t} \Omega_t(t) P_{bf \to f} \Omega_f(t)$$

In the tibial landmark by:

$$[\Omega_{t/f}]_t(t) = P_{bt \to t} \Omega_t(t) - P_{f \to t}(t) P_{bf \to f} \Omega_f(t)$$

Equipment and System

According to a second aspect, the invention in particular relates to the equipment $2a$, $2b$, $3$, $4$ for the implementation of one or the other of the embodiments of the method.

As explained previously, according to a first embodiment the equipment is a first or a second autonomous box $2a$, $2b$ comprising the first or the second inertial measuring means $20a$, $20b$ and the data processing means $21$ configured for the implementation of the steps of the method.

Each box $2a$, $2b$ further comprises means for attaching $23$ the box $2$ to the lower limb $10$ (respectively to the leg or to the thigh), and if need be data storage means $22$ (for the storage of the measured accelerations/angular velocities or the estimated movements) and/or communication means $25$ for the exportation of the results.

According to a second embodiment, the equipment is a mobile terminal $3$ or a server $4$, suited to communicate with each box $2a$, $2b$ comprising inertial measuring means $20a$, $20b$. In other words, the terminal $3$ or the server $4$ comprises the processing means $31$ or $41$ configured for the implementation of the steps of the method. Each box $2a$, $2b$ may all the same comprise data processing means $21$ for the control of the means $20a$, $20b$ and the transmission (via communication means $25$) of the measured data to the data processing means $31$, $41$.

It should be noted that the means $21$, $31$, $41$ can if need be share the steps of the method.

The invention also relates to in this case the system comprising the equipment $3$, $4$ according to this embodiment and the "satellite" boxes $2a$, $2b$ in connection In all cases, the data processing means $21$, $31$, $41$ of the "main" equipment $2a$, $2b$, $3$, $4$ are configured to implement:

a first module for receiving, during at least one reference movement of said lower limb $10$ from a reference position, a reference acceleration and a reference angular velocity of said tibia $11a$ acquired by the first inertial measuring means $20a$ integral with the tibia $11a$ of said lower limb $10$, and a reference acceleration and a reference angular velocity of said femur $11b$ acquired by the second inertial measuring means $20b$ integral with the femur $11b$, a first module for estimating a plurality of morphological parameters of said lower limb $10$, as a function of said measured reference accelerations and reference angular velocities;

a module for determining a relative orientation in said initial position between said tibia $11a$ and femur $11b$, as a function of said estimated morphological parameters of said lower limb $10$;

a second module for receiving, during the working movement of said lower limb from said initial position, a working angular velocity of said tibia $11a$ acquired by the first inertial measuring means $20a$, and a working angular velocity of said femur $11b$ acquired by the second inertial measuring means $20b$;

A second module for estimating the relative orientation between said tibia $11a$ and femur $11b$ as a function of said measured working angular velocities, and of said relative orientation in said initial position between said tibia $11a$ and femur $11b$.

Computer Programme Product

According to a third and a fourth aspect, the invention relates to a computer programme product comprising code instructions for the execution (on the processing means $21$, $31$, $41$) of a method for estimating the relative orientation between a tibia $11a$ and a femur $11b$ of a lower limb $10$ of a person $1$ according to the first aspect of the invention, as well as storage means that can be read by a computer equipment (for example data storage means $22$) in which this computer programme product is installed.

The invention claimed is:

1. Method for estimating the relative orientation between a tibia and a femur of a lower limb of a person during a working movement of said lower limb from an initial position, the method being characterised in that it comprises the steps of:
(a) During at least one reference movement of said lower limb from a reference position having a same relative orientation between the tibia and the femur as the initial position, acquiring by first inertial measuring means affixed to the tibia of said lower limb a reference acceleration and a reference angular velocity of said tibia, and acquiring by second inertial measuring means affixed to the femur a reference acceleration and a reference angular velocity of said femur;
(b) Estimating by a data processor a plurality of morphological parameters of said lower limb, as a function of said measured reference accelerations and reference angular velocities;
(c) Determining by the data processor a relative orientation in said initial position between said tibia and femur, as a function of said estimated morphological parameters of said lower limb;
(d) During said working movement of said lower limb from the initial position, acquiring by the first inertial measuring means a working angular velocity of said tibia, and acquiring by the second inertial measuring means a working angular velocity of said femur;

(e) Estimating by the data processor the relative orientation between said tibia and femur as a function of said measured working angular velocities, and of said relative orientation in said initial position between said tibia and femur.

2. Method according to claim 1, wherein step (c) comprises the determination from the morphological parameters:
of a relative orientation $P_{t \to bt}$ between the first inertial measuring means and the tibia;
of a relative orientation $P_{bf \to f}$ between the second inertial measuring means and the femur;
of a relative orientation in said initial position $P_{bf^0 \to bt^0}$ between the first inertial measuring means and the second inertial measuring means;
from which is expressed said relative orientation in said initial position $P_{t \to f}(0)$ between said tibia and femur.

3. Method according to claim 2, wherein step (e) comprises the determination of the variation in relative orientation $P_{bt^0 \to bt}(t)$ of the first inertial measuring means with respect to the initial position, and the determination of the variation in relative orientation $P_{bf^0 \to bf}(t)$ of the second inertial measuring means with respect to the initial position, the relative orientation $P_{t \to f}(t)$ between said tibia and femur being given by the equation $$P_{t \to f}(t) = P_{bf \to f} P_{bf^0 \to bf}(t) P_{bt^0 \to bf^0} P_{bt \to bt^0}(t) P_{t \to bt}$$

4. Method according to claim 1, wherein said plurality of estimated morphological parameters comprises the position of the centre of a knee of the lower limb, the position of the centre of a hip of the lower limb, the position of the centre of an ankle of the lower limb, the inter-malleolar direction of the ankle of the lower limb, and the average direction of rotation of the tibia with respect to the femur in the course of a flexion movement.

5. Method according to claim 4, wherein step (a) is implemented for at least one reference movement comprising the palpation of the lower limb by a tool so as to estimate via said palpation the position of the centre of a knee of the lower limb and/or the position of the centre of an ankle of the lower limb.

6. Method according to claim 4, wherein said plurality of estimated morphological parameters also comprises the mechanical axis of the femur, the mediolateral axis of the femur, the anteroposterior axis of the femur, the mechanical axis of the tibia, the mediolateral axis of the tibia, the anteroposterior axis of the tibia, estimated in step (b) from said position of the centre of the knee of the lower limb, position of the centre of the hip of the lower limb, position of the centre of the ankle of the lower limb, inter-malleolar direction of the ankle of the lower limb and average direction of rotation of the tibia with respect to the femur in the course of a flexion movement.

7. Method according to claim 6, wherein step (c) comprises the determination from the morphological parameters:
of a relative orientation $P_{t \to bt}$ between the first inertial measuring means and the tibia;
of a relative orientation $P_{bf \to f}$ between the second inertial measuring means and the femur;
wherein—the relative orientation $P_{t \to bt}$ between the first inertial measuring means and the tibia is determined from said mechanical axis of the tibia, mediolateral axis of the tibia and anteroposterior axis of the tibia; and—the relative orientation $P_{f \to bf}$ between the second inertial measuring means and the femur is determined from said mechanical axis of the femur, mediolateral axis of the femur and anteroposterior axis of the femur.

8. Method according to claim 1, comprising the implementation of step (a) for a plurality of reference movements including at least:
a circular movement of the lower limb maintained rigid such that the orientation between the tibia and the femur is permanently identical to that in the reference position, the hip being maintained immobile;
a circular movement of a leg of the lower limb, the knee being maintained immobile;
a flexion movement of the lower limb from the reference position.

9. Method according to claim 8, wherein step (c) comprises the determination from the morphological parameters of a relative orientation in said initial position $P_{bf^0 \to bt^0}$ between the first inertial measuring means and the second inertial measuring means, wherein said relative orientation in said initial position $P_{bf^0 \to bt^0}$ between the first inertial measuring means and the second inertial measuring means is determined by solving Wahba's problem during said circular movement of the lower limb maintained rigid.

10. Method according to claim 8, wherein said plurality of estimated morphological parameters comprises the position of the centre of a knee of the lower limb, the position of the centre of a hip of the lower limb, wherein the position of the centre of a knee of the lower limb and/or the position of the centre of a hip of the lower limb is estimated at step (b) as the centre of rotation of the first and/or of the second inertial measuring means in the course of one of said circular movements by the least squares resolution of an equation linking said measured reference accelerations and reference angular velocities.

11. Equipment for estimating the relative orientation between a tibia and a femur of a lower limb of a person during a working movement of said lower limb from an initial position, characterised in that it comprises a data processor configured to implement:
receiving, during at least one reference movement of said lower limb from a reference position having a same relative orientation between the tibia and the femur as the initial position, a reference acceleration and a reference angular velocity of said tibia acquired by first inertial measuring means affixed to the tibia of said lower limb, and a reference acceleration and a reference angular velocity of said femur acquired by second inertial measuring means affixed to the femur;
estimating a plurality of morphological parameters of said lower limb, as a function of said measured reference accelerations and reference angular velocities;
determining a relative orientation in said initial position between said tibia and femur, as a function of said estimated morphological parameters of said lower limb;
receiving, during said working movement of said lower limb from the initial position, a working angular velocity of said tibia acquired by the first inertial measuring means, and a working angular velocity of said femur acquired by the second inertial measuring means;
estimating the relative orientation between said tibia and femur as a function of said measured working angular velocities, and of said relative orientation in said initial position between said tibia and femur.

12. Equipment according to claim 11, enclosed in a box comprising the first or the second inertial measuring means.

13. Equipment according to claim 11, comprising a mobile terminal or a server, suited to communicate with a first box comprising the first inertial measuring means and a second box comprising the second inertial measuring means.

14. System comprising the equipment according to claim 13 and at least one first and one second box in connection.

15. A non-transitory computer-readable medium comprising instructions stored thereon for execution by a processor of a method for estimating the relative orientation between a tibia and a femur of a lower limb of a person, wherein the instructions configure the processor to perform acts comprising:

During at least one reference movement of said lower limb from a reference position having a same relative orientation between the tibia and the femur as an initial position, acquiring by first inertial measuring means affixed to the tibia of said lower limb a reference acceleration and a reference angular velocity of said tibia, and acquiring by second inertial measuring means affixed to the femur a reference acceleration and a reference angular velocity of said femur;

Estimating a plurality of morphological parameters of said lower limb, as a function of said measured reference accelerations and reference angular velocities;

Determining a relative orientation in said initial position between said tibia and femur, as a function of said estimated morphological parameters of said lower limb;

During said working movement of said lower limb from the initial position, acquiring by the first inertial measuring means a working angular velocity of said tibia, and acquiring by the second inertial measuring means a working angular velocity of said femur;

Estimating the relative orientation between said tibia and femur as a function of said measured working angular velocities, and of said relative orientation in said initial position between said tibia and femur.

* * * * *